US012721845B2

(12) United States Patent
Uchida et al.

(10) Patent No.: US 12,721,845 B2
(45) Date of Patent: Sep. 1, 2026

(54) THERAPEUTIC OR PROPHYLACTIC AGENT FOR CACHEXIA ACCOMPANIED BY GHRELIN RESISTANCE

(71) Applicant: Toray Industries, Inc., Tokyo (JP)

(72) Inventors: Masashi Uchida, Kamakura (JP); Yu Omori, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 327 days.

(21) Appl. No.: 18/286,379

(22) PCT Filed: Apr. 22, 2022

(86) PCT No.: PCT/JP2022/018548

§ 371 (c)(1),
(2) Date: Oct. 11, 2023

(87) PCT Pub. No.: WO2022/225045

PCT Pub. Date: Oct. 27, 2022

(65) Prior Publication Data

US 2024/0197718 A1 Jun. 20, 2024

(30) Foreign Application Priority Data

Apr. 23, 2021 (JP) ................................. 2021-073026

(51) Int. Cl.
*A61K 31/485* (2006.01)
*A61P 21/00* (2006.01)

(52) U.S. Cl.
CPC ............ *A61K 31/485* (2013.01); *A61P 21/00* (2018.01)

(58) Field of Classification Search
None
See application file for complete search history.

(56) References Cited

U.S. PATENT DOCUMENTS 4,760,069 A 7/1988 Rzeszotarski et al.
6,277,859 B1 8/2001 Nagase et al.
(Continued)

FOREIGN PATENT DOCUMENTS

EP 4 049 658 A1 8/2022
JP 2010-509343 A 3/2010
(Continued)

OTHER PUBLICATIONS

Miyazaki et al., Molecular Nutrition & Food Research, 58 (10) (2014), pp. 2046-20 (Year: 2014).*
(Continued)

*Primary Examiner* — Jeffrey S Lundgren
*Assistant Examiner* — Anthony Joseph Seitz
(74) *Attorney, Agent, or Firm* — DLA Piper LLP (US)

(57) ABSTRACT

There is a problem of providing a therapeutic or prophylactic agent for cachexia accompanied by ghrelin resistance. The therapeutic or prophylactic agent for cachexia accompanied by ghrelin resistance contains, as an active ingredient, an opioid κ receptor agonist compound represented by the formula (I):

(I)

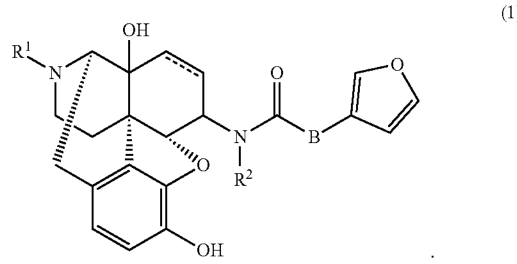

5 Claims, 4 Drawing Sheets

(56) References Cited

U.S. PATENT DOCUMENTS

| | | | | |
|---|---|---|---|---|
| 9,006,262 | B2 * | 4/2015 | Suzuki | A61P 35/00 514/289 |
| 2007/0238662 | A1 | 10/2007 | Mintz | |
| 2013/0310414 | A1 | 11/2013 | Suzuki et al. | |
| 2023/0255955 | A1 * | 8/2023 | Omori | A61P 21/00 514/289 |
| 2024/0139176 | A1 * | 5/2024 | Omori | A61K 31/454 |

FOREIGN PATENT DOCUMENTS

| | | | |
|---|---|---|---|
| JP | 2018-62488 | A | 4/2018 |
| WO | 93/15081 | A1 | 8/1993 |
| WO | 05/097261 | A1 | 10/2005 |
| WO | 2008/057608 | A2 | 5/2008 |
| WO | 2012/105475 | A1 | 8/2012 |
| WO | 2021/079978 | A1 | 4/2021 |

OTHER PUBLICATIONS

Kenneth A. Kern, M.D. et al., "Cancer Cachexia," Journal of Parenteral and Enteral Nutrition, 1988, vol. 12, No. 3, pp. 286-298.
T.D. Steele et al., "Nocturnal Depletion of Hypothalamic Dynorphin in Anorexic Walker-256 Tumor-Bearing Rats," Pharmacology Biochemistry & Behavior, 1988, vol. 29, pp. 541-545.
Kristine A. Nelson et al., "The Cancer Anorexia-Cachexia Syndrome," Journal of Clinical Oncology, Jan. 1994, vol. 12, No. 1, pp. 213-225.
Masamitsu Nakazato et al., "A role for ghrelin in the central regulation of feeding," Nature, Jan. 11, 2001, vol. 409, pp. 194-198.
Yoshito Shimizu et al., "Increased Plasma Ghrelin Level in Lung Cancer Cachexia," Clinical Cancer Research, Feb. 2003, vol. 9, pp. 774-778.
Masayasu Kojima et al., "Ghrelin: Structure and Function," Physiological Reviews, 2005, vol. 85, pp. 495-522.
R. Northrup et al., "Effect of ghrelin and anamorelin (ONO-7643), a selective ghrelin receptor agonist, on tumor growth in a lung cancer mouse xenograft model," Supportive Care in Cancer, 2013, vol. 21, pp. 2409-2415.
Claudio Pietra et al., "Anamorelin HC1 (ONO-7643), a novel ghrelin receptor agonist, for the treatment of cancer anorexia-cachexia syndrome: preclinical profile," Journal of Cachexia, Sarcopenia and Muscle, 2014, vol. 5, pp. 329-337.
Nalfurafine Hydrochloride, Attachment to the application for marketing approval of drugs, https://www.pmda.go.jp/drugs/2014/P201400168/.
Kiyoshi Terawaki et al., "Development of ghrelin resistance in a cancer cachexia rat model using human gastric cancer-derived 85As2 cells and the palliative effects of the Kampo medicine rikkunshito on the model," Plos One, Mar. 1, 2017, vol. 12, No. 3, pp. 1-25.
Tateaki Naito, "Evaluation of the True Endpoint of Clinical Trials for Cancer Cachexia," Asia-Pacific Journal of Oncology Nursing, 2019, vol. 6, pp. 227-233.
International Search Report dated Jun. 7, 2022 in counterpart International Application No. PCT/JP2022/018548 (English).
Written Opinion dated Jun. 7, 2022 in counterpart International Application No. PCT/JP2022/018548.
Office Action dated Sep. 23, 2025, from counterpart Taiwanese Application No. 111115371.
Amparo Romero-Picó et al., "Hypothalamic κ-Opioid Receptor Modulates the Orexigenic Effect of Ghrelin," Neuropsychopharmacology, Jan. 24, 2013, vol. 38, pp. 1296-1307.
Office Action dated Nov. 8, 2025, of counterpart Chinese Application No. 202280029314.7, along with an English translation.

* cited by examiner

THERAPEUTIC OR PROPHYLACTIC AGENT FOR CACHEXIA ACCOMPANIED BY GHRELIN RESISTANCE

TECHNICAL FIELD

This disclosure relates to a therapeutic or prophylactic agent for cachexia accompanied by ghrelin resistance.

BACKGROUND

Cachexia is a complex syndrome of metabolic abnormality caused in association with an underlying disease, and is defined as muscle loss irrespective of fat loss. Examples of the underlying disease which causes cachexia include chronic diseases such as malignant tumors, tuberculosis, diabetes, blood diseases, endocrine diseases, infectious diseases, and acquired immunodeficiency syndrome. Cachexia is known as a prominent systemic syndrome having prominent symptoms such as weight loss, anemia, edema, anorexia, general debility, and malaise (Kern et al., Journal of Parenteral and Enteral Nutrition, 1988, Vol. 12, pp. 286-298).

In the past, ghrelin administration aimed at improvement in cachectic symptoms has been examined. Ghrelin is a peptide hormone discovered as an endogenous ligand (GHSR agonist) for a growth hormone secretagogue receptor (GHSR). Ghrelin is produced mainly in stomachs through GHSR in human and animals to enhance growth hormone secretion (Kojima, Kanagawa, Physiological Reviews, 2005, Vol. 85, pp. 495-522). It is reported that ghrelin has a variety of effects such as increase of food intake (improvement of eating disorder), enhancement of gastric acid secretion and gastric peristalsis, and increase of skeletal muscle (Kojima, Kanagawa, Physiological Reviews, 2005, Vol. 85, pp. 495-522).

As a cachexia therapeutic agent available in Japan, anamorelin hydrochloride, which is a ghrelin derivative and also a GHSR agonist, is known as an only cachexia therapeutic agent in non-small cell lung cancer, gastric cancer, pancreatic cancer, and colorectal cancer (International Publication No. WO 05/097261).

Meanwhile, it has been reported that ghrelin concentration in blood is increased in patients at the advanced stage of cachexia and impaired ghrelin response, namely, ghrelin resistance is caused (Nakazato et al., Nature, 2001, Vol. 409, pp. 194-198).

A type of cachexia is cachexia derived from malignant tumors as the underlying disease, which is referred to as cancer cachexia. It has been reported that an increase in ghrelin concentration in blood and impaired ghrelin response are caused more frequently in patients with cancer cachexia, compared with common cancer patients (Shimizu et al., Clin. Cancer Res., 2003, Vol. 9, pp. 774-778). It has also been reported that an increase in ghrelin concentration in blood is caused depending on the progression of pathological conditions of cachexia in cancer patients (Shimizu et al., Clin. Cancer Res., 2003, Vol. 9, pp. 774-778).

A majority of cancer patients suffer from cancer cachexia. The number of patients with cancer cachexia is large, and cancer cachexia is said to account for approximately 20% of causes of death from malignant tumors. Physical strength of a patient with cancer cachexia is significantly lost as the symptoms become worsened. Accordingly, it is impossible to continue treatment with antitumor agents and responses to antitumor agents are also lowered.

As described above, cancer cachexia causes complicated metabolic disorders. If a patient merely receives nutritional support to improve the nutritional status thereof, accordingly, the pathological conditions of the patient would not always be improved, and nutritional support may accelerate exacerbation of malignant tumors, disadvantageously. In addition, physical strength of a patient is lost to a significant extent as cancer cachexia advances. This makes treatment with highly toxic antitumor agents impossible in general, and development of cancer cachexia interferes treatment of malignant tumors. Even if a patient has sufficient physical strength and administration of antitumor agents to a patient is possible, in general, side effects such as bone marrow toxicity caused by an antitumor agent would occur, and the cancer cachectic symptoms would not be improved (Nelson et al., Journal of Clinical Oncology, 1994, Vol. 12, pp. 213-225).

As described above, ghrelin resistance may have been developed in patients with advanced cachexia. Accordingly, a GHSR agonist (e.g., anamorelin hydrochloride) may be less likely to exert its effects on some patients. For example, Rikkunshito, a traditional Japanese herbal medicine, partially improves the ghrelin resistance of patients with advanced cachexia, which suggests a therapeutic potential to cancer cachexia (Terawaki et al., PLos One, 2017, Vol. 12, p. e0173113).

On the other hand, a compound having a morphinan skeleton or a pharmacologically acceptable acid addition salt thereof having opioid κ receptor agonistic properties and applications thereof as a pain reliever and a diuretic agent are disclosed (International Publication No. WO 93/015081). Applications thereof as a cachexia therapeutic agent (International Publication No. WO 12/105475) are also disclosed.

Anamorelin hydrochloride, which is a cancer cachexia therapeutic agent, is confirmed to express no drug efficacy in animal models of ghrelin resistance in which ghrelin concentration in blood is increased in the examples below. In addition, Rikkunshito, which may partially improve the ghrelin resistance, is a traditional Japanese herbal medicine. To use Rikkunshito as a first-choice drug, accordingly, therapeutic evidences that are more precise than those of medicines are necessary, and use thereof is considered difficult. That is, many problems such as the development of medical education remain unsolved.

In the past, there is no report, such that a compound having opioid κ receptor agonistic properties would exert therapeutic or prophylactic effects on cachexia accompanied by ghrelin resistance. In addition, there is no suggestion, such that a compound having a morphinan skeleton or a pharmacologically acceptable acid addition salt thereof would exert therapeutic or prophylactic effects on cachexia accompanied by ghrelin resistance.

In palliative therapy such as treatment of cachexia, it is considered desirable that there are many therapeutic agents of different mechanisms and that adequate therapy is provided for each patient. Accordingly, continuous development of therapeutic agents based on novel mechanisms is needed.

It could therefore be helpful to provide a therapeutic or prophylactic agent for cachexia accompanied by ghrelin resistance.

SUMMARY

We found that a compound having opioid κ receptor agonistic properties, preferably a particular compound having a morphinan skeleton, would have a therapeutic or prophylactic effect on cachexia accompanied by ghrelin resistance, and have completed this disclosure.

We thus provide a therapeutic or prophylactic agent for cachexia accompanied by ghrelin resistance comprising, as an active ingredient, an opioid κ receptor agonistic compound.

The opioid κ receptor agonistic compound is preferably a compound represented by General Formula (I) or a pharmacologically acceptable acid addition salt thereof:

(1)

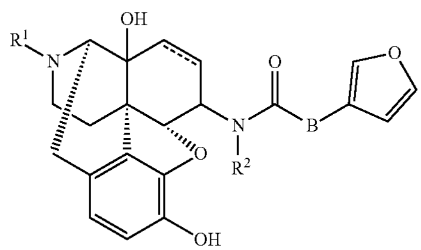

A double line composed of a dotted line and a solid line represents a double bond or a single bond, $R^1$ represents a cycloalkylalkyl having 4 to 7 carbon atoms, $R^2$ represents a linear or branched alkyl having 1 to 5 carbon atoms, and B represents a —CH═CH—.

In the compound represented by General Formula (I), preferably, $R^1$ is a cyclopropylmethyl, a cyclobutylmethyl, a cyclopentylmethyl, or a cyclohexylmethyl, and $R^2$ is a methyl, an ethyl, or a propyl; more preferably, $R^1$ is a cyclopropylmethyl, $R^2$ is a methyl, and B is a trans-form —CH═CH—.

The compound represented by General Formula (I) is more preferably (−)-17-(cyclopropylmethyl)-3,14β-dihydroxy-4,5α-epoxy-6β-[N-methyl-trans-3-(3-furyl)acrylamide]morphinan exemplified below:

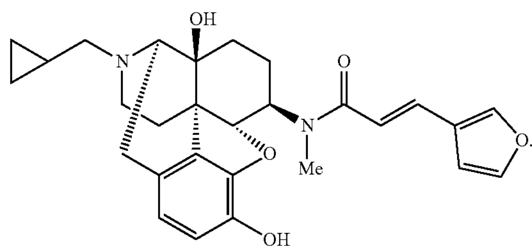

A high therapeutic or prophylactic effect to cachexia accompanied by ghrelin resistance can be expected.

The opioid κ receptor agonistic compound is preferably a compound represented by General Formula (II) or a pharmacologically acceptable acid addition salt:

(II)

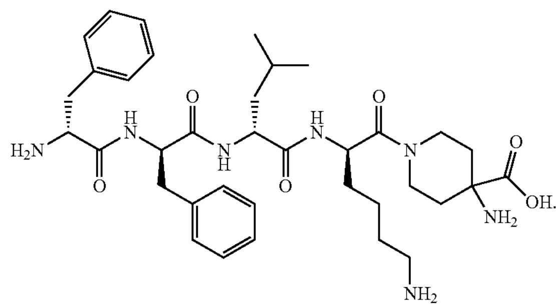

The therapeutic or prophylactic agent for cachexia accompanied by ghrelin resistance is preferably a therapeutic or prophylactic agent for cancer cachexia accompanied by ghrelin resistance.

An example of the cachexia accompanied by ghrelin resistance is cachexia in a state such that a GHSR agonist such as anamorelin hydrochloride would not produce a response. Specifically, we provide a therapeutic or prophylactic agent for cachexia in a state such that a GHSR agonist such as anamorelin hydrochloride would not produce a response, which comprises, as an active ingredient, an opioid κ receptor agonistic compound. The preferable aspect concerning the opioid κ receptor agonistic compound is also applicable to the aspect described above.

We also provide a pharmaceutical composition for treating or preventing cachexia accompanied by ghrelin resistance, which comprises the opioid κ receptor agonistic compound and a pharmaceutically acceptable carrier. The preferable aspect concerning the opioid κ receptor agonistic compound is also applicable to the present aspect.

We further provide use of the opioid κ receptor agonistic compound for treating or preventing cachexia accompanied by ghrelin resistance. The preferable aspect concerning the opioid κ receptor agonistic compound is also applicable to the present aspect.

We still further provide the opioid κ receptor agonistic compound for use in treating or preventing cachexia accompanied by ghrelin resistance. The preferable aspect concerning the opioid κ receptor agonistic compound is also applicable to the present aspect.

We further yet provide use of the opioid κ receptor agonistic compound in the manufacture of a medicament for treating or preventing cachexia accompanied by ghrelin resistance (such as the therapeutic or prophylactic agent for cachexia accompanied by ghrelin resistance). The preferable aspect concerning the opioid κ receptor agonistic compound is also applicable to the present aspect.

We still further yet provide a method of treating or preventing cachexia accompanied by ghrelin resistance, which comprises a step of administering the opioid κ receptor agonistic compound to a patient in need of treatment or prevention of cachexia accompanied by ghrelin resistance. The preferable aspect concerning the opioid κ receptor agonistic compound is also applicable to the present aspect.

Our opioid κ receptor agonistic compound can improve symptoms of cachexia accompanied by ghrelin resistance.

DETAILED DESCRIPTION

Figure 1:
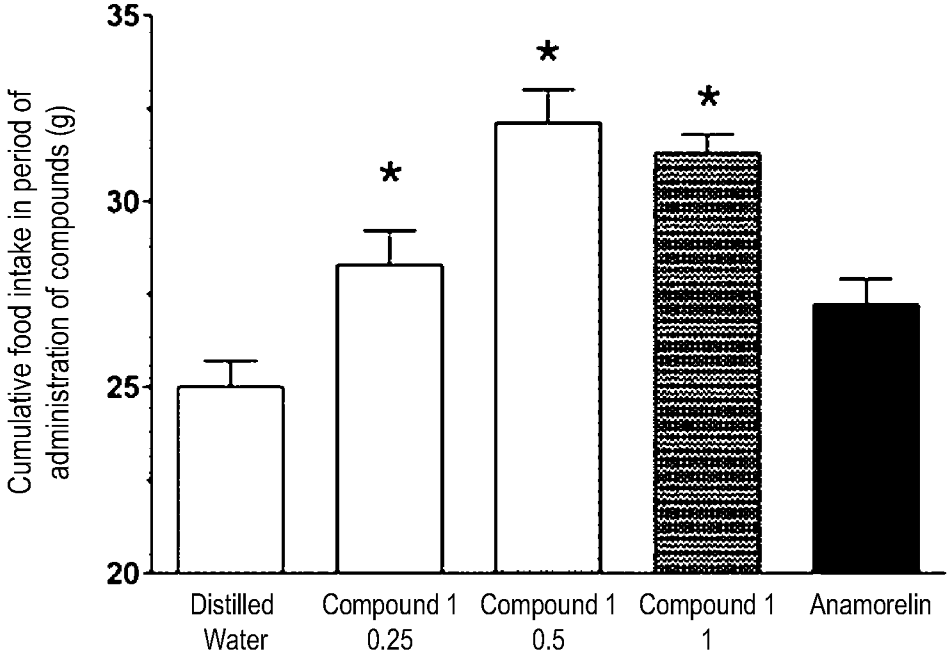
FIG. 1 is a graph showing the increasing effect in cumulative food intake by administration of Compound 1 in a tumor-bearing mouse model (non-small cell lung cancer model accompanied by ghrelin resistance).

Our therapeutic or prophylactic agent for cachexia accompanied by ghrelin resistance comprises, as an active ingredient, an opioid κ receptor agonistic compound.

As opioid receptors, μ receptor, δ receptor, and κ receptor are known, and endogenous substances and synthesized compounds that selectively stimulate relevant receptors are known. The chemical structure of the opioid κ receptor agonistic compound is not particularly limited herein, provided that such compound exerts agonistic properties on the opioid κ receptor, with a selective agonistic compound for the opioid κ receptor being preferable. The term "selective agonistic compound for the opioid κ receptor" refers to a κ receptor-selective compound relative to the μ receptor and the δ receptor. A κ receptor-selective compound shows higher agonistic properties on the κ receptor compared to the agonistic properties on the μ receptor or the δ receptor. Such κ receptor-selective compound preferably shows 2 times or greater agonistic properties on the human κ receptor compared to the agonistic properties on the human μ receptor or δ receptor, more preferably 10 times or greater, further preferably 100 times or greater, and most preferably 200 times or greater (Nalfurafine Hydrochloride, the documents attached to the application for grant of approval to manufacture the new drugs, https://www.pmda.go.jp/drugs/2014/P201400168/).

In an example, the opioid κ receptor agonistic compound is preferably a compound represented by General Formula (I) or a pharmacologically acceptable acid addition salt thereof:

(1)

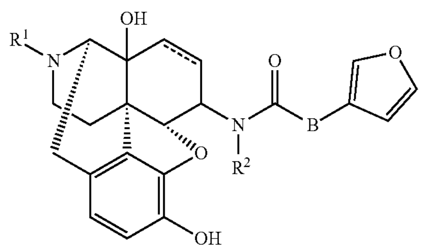

A double line composed of a dotted line and a solid line represents a double bond or a single bond, $R^1$ represents a cycloalkylalkyl having 4 to 7 carbon atoms, $R^2$ represents a linear or branched alkyl having 1 to 5 carbon atoms, and B represents a —CH═CH—.

In General Formula (I), $R^1$ is preferably a cyclopropylmethyl, a cyclobutylmethyl, a cyclopentylmethyl, or a cyclohexylmethyl, and more preferably a cyclopropylmethyl.

$R^2$ is preferably a methyl, an ethyl, or a propyl, and more preferably a methyl.

B is preferably a trans-form —CH═CH—.

The compound represented by General Formula (I) is further preferably a (−)-form compound where the double line composed of a dotted line and a solid line is a single bond, $R^1$ is a cyclopropylmethyl, $R^2$ is a methyl, and B is a trans-form —CH═CH—, namely, (−)-17-(cyclopropylmethyl)-3,14β-dihydroxy-4,5α-epoxy-6β-[N-methyl-trans-3-(3-furyl)acrylamide]morphinan represented by the formula below:

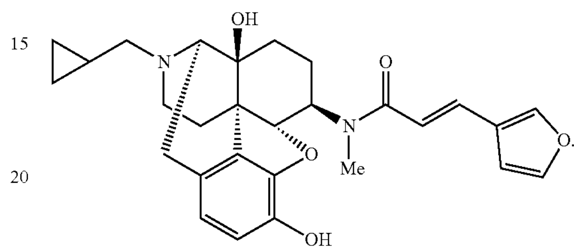

In a preferred example, the compound represented by General Formula (I) or a pharmacologically acceptable acid addition salt thereof may be (−)-17-(cyclopropylmethyl)-3,14β-dihydroxy-4,5α-epoxy-6β-[N-methyl-trans-3-(3-furyl)acrylamide]morphinan or a pharmacologically acceptable acid addition salt thereof. An example of the (−)-17-(cyclopropylmethyl)-3,14β-dihydroxy-4,5α-epoxy-6β-[N-methyl-trans-3-(3-furyl)acrylamide]morphinan or a pharmacologically acceptable acid addition salt thereof is (−)-17-(cyclopropylmethyl)-3,14β-dihydroxy-4,5α-epoxy-6β-[N-methyl-trans-3-(3-furyl)acrylamide]morphinanhydrochloride.

In another example, the opioid κ receptor agonistic compound is preferably a compound represented by General Formula (II) or a pharmacologically acceptable acid addition salt thereof:

(II)

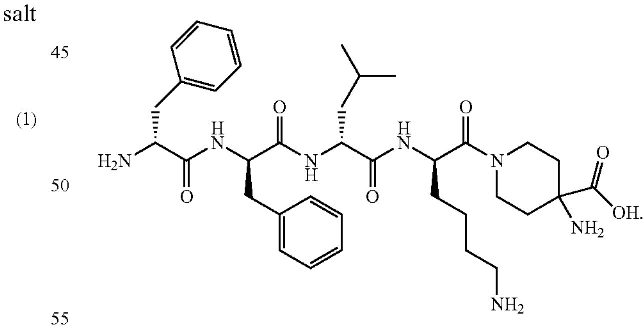

In a preferred example, General Formula (II) or a pharmacologically acceptable acid addition salt thereof may be difelikefalin(4-amino-1-[(2R)-6-amino-2-[(2R)-2-[(2R)-2-[(2R)-2-amino-3-phenylpropanamide]-3-phenylpropanamide]-4-methylpentanamide]hexanoyl]piperidine-4-carboxylic acid) or a pharmacologically acceptable acid addition salt thereof, and an example of the difelikefalin or a pharmacologically acceptable acid addition salt thereof is difelikefalin acetate.

The following terms are defined as follows unless otherwise stated.

Examples of the "pharmacologically acceptable acid addition salt" of the compounds represented by General Formulae (I) and (II) include a salt with an inorganic acid and a salt with an organic acid. Examples of the salt with an inorganic acid include hydrochloride, sulfate, nitrate, hydrobromate, hydroiodide and phosphate, and examples of the salt with an organic acid include oxalate, malonate, citrate, fumarate, lactate, malate, succinate, tartrate, acetate, trifluoroacetate, maleate, gluconate, benzoate, ascorbate, glutarate, mandelate, phthalate, methanesulfonate, ethanesulfonate, benzenesulfonate, p-toluenesulfonate, camphorsulfonate, aspartate, glutamate and cinnamate. Of these, hydrochloride, hydrobromate, phosphate, tartrate, methanesulfonate and the like are preferably used.

The compounds represented by General Formulae (I) and (II) or a pharmacologically acceptable acid addition salt thereof may be an anhydride or a solvate, or may form a crystal polymorphism. The solvate herein may be a hydrate or a nonhydrate, but a pharmacologically acceptable solvate is preferable.

The compound represented by General Formula (I) or a pharmacologically acceptable acid addition salt thereof can be produced, for example, in accordance with a known synthesis method (WO 93/015081).

The compound represented by General Formula (II) can be produced, for example, in accordance with a known synthesis method (WO 08/057608).

The "cachexia" includes systemic syndromes having prominent symptoms such as weight loss, anemia, edema, anorexia, general debility, and malaise in chronic diseases such as malignant tumors, tuberculosis, diabetes, blood diseases, endocrine diseases, infectious diseases, and acquired immunodeficiency syndromes. Examples thereof include cancer cachexia, tuberculous cachexia, diabetic cachexia, blood disease-derived cachexia, endocrine disease-derived cachexia, infectious disease-derived cachexia, and cachexia derived from acquired immunodeficiency syndrome. The therapeutic or prophylactic agent for cachexia accompanied by ghrelin resistance is preferably used on cachexia caused by malignant tumors (sometimes cancer cachexia) among these types of cachexia.

The "malignant tumor" (also cancer or malignant neoplasm) includes epithelial tissue-derived "cancer," non-epithelial tissue-derived "sarcoma," and those derived from hemopoietic organs. Examples thereof include malignant melanoma, malignant bone tumor, gastric cancer, hepatocyte cancer, acute myeloid leukemia, acute lymphocytic leukemia, uterine cervical cancer, uterine cancer, esophagus cancer, pancreatic cancer, prostate cancer, colorectal cancer, breast cancer, lung cancer, bladder cancer, and ovarian cancer.

The therapeutic or prophylactic agent for cachexia accompanied by ghrelin resistance has effect to improve prominent systemic syndromes accompanied by impaired ghrelin response such as weight loss, anemia, edema, anorexia, general debility, and malaise, which are expressed in chronic diseases such as malignant tumor, tuberculosis, diabetes, blood diseases, endocrine disease, infectious disease, and acquired immunodeficiency syndromes. As a result, symptoms of cachexia accompanied by ghrelin resistance can be improved. In particular, weight loss is known as the most critical end point that occurs prior to the advancement of cachectic conditions (the evaluation item to demonstrate efficacy of the therapy) (Asia-Pacific Journal of Oncology Nursing, 2019, Vol. 6, pp. 227-233). Concerning anamorelin hydrochloride, in fact, an increase in fat-free body weight and an increase in appetite are approved as the primary evaluation item and the secondary evaluation item, respectively.

In the therapeutic or prophylactic agent for cachexia accompanied by ghrelin resistance, the opioid κ receptor agonistic compound is preferably used in accordance with the dosage and administration regimen that would not develop side effects such as addiction or aversion. The dosage and administration regimen that would not develop side effects is more preferably the dosage and administration regimen that would not develop addiction, and further preferably the dosage and administration regimen that would develop neither addiction nor aversion (Nalfurafine Hydrochloride).

The term "ghrelin resistance" refers to impaired ghrelin response. Ghrelin is not limited herein, provided that it indicates a GHSR agonist and has GHSR agonistic activity. Ghrelin is preferably a ghrelin derivative and more preferably anamorelin hydrochloride. When ghrelin response is impaired, ghrelin would not exert desired pharmacological activity. It is preferable that a ghrelin derivative do not exert desired drug efficacy, it is more preferable that anamorelin hydrochloride do not exert desired drug efficacy, and it is further preferable that anamorelin hydrochloride do not exert desired drug efficacy in accordance with the designated dosage and administration regimen. In clinical setting, for example, an increase is observed in ghrelin concentration in blood of a patient with ghrelin resistance. That is, "ghrelin resistance" preferably indicates an increase in ghrelin concentration in blood.

Whether or not the opioid κ receptor agonistic compound is effective for treatment or prevention of cachexia accompanied by ghrelin resistance can be evaluated based on, for example, the increasing effect in body weight or the increasing effect in food intake of the compound as the indicators. Whether or not the animal model has ghrelin resistance can be determined by verifying that anamorelin hydrochloride, which is a GHSR agonist at an adequate dose, would not exert effects on the indicator. Concerning an adequate dose of anamorelin hydrochloride, use of anamorelin hydrochloride at 30 mg/kg would lead to an increase in body weight of a normal animal in addition to a model of non-small cell lung cancer to which A549 cells have been transplanted subcutaneously in the abdominal region. Thus, a model is determined to have ghrelin resistance when anamorelin hydrochloride does not exert its effects at 30 mg/kg (Support Care Cancer, 2013, Vol. 21, pp. 2409-2415; Journal of Cachexia, Sarcopenia and Muscle, 2014, Vol. 5, pp. 329-337).

The therapeutic or prophylactic agent for cachexia accompanied by ghrelin resistance can be used as a therapeutic or prophylactic agent for cachexia for mammals (such as humans, mice, rats, rabbits, dogs, cats, bovines, horses, pigs, and monkeys).

When the opioid κ receptor agonistic compound is clinically used as the therapeutic or prophylactic agent for cachexia accompanied by ghrelin resistance, the opioid κ receptor agonistic compound can be used as it is, or can be administered orally or parenterally by suitably mixing with, as a pharmacologically acceptable carrier, additives such as an excipient, a capsule membrane, a stabilizer, a preservative, a buffer, a solubilizer, an emulsifier, a diluent, a tonicity agent, a disintegrator, a lubricant, a coating agent, a plasticizer or a coloring agent.

Examples of the above excipient include D-mannitol, erythritol, lactose and macrogol. Examples of the above capsule membrane include gelatin and succinylated gelatin.

Examples of the above stabilizer include sodium thiosulfate hydrate. Examples of the above disintegrator include crospovidone, low substituted hydroxypropylcellulose, croscarmellose sodium, carmellose calcium, and sodium carboxymethyl starch. Examples of the above lubricant include magnesium stearate, sodium stearyl fumarate and sucrose fatty acid ester. Examples of the above coating agent include hydroxypropylmethylcellulose and polyvinyl alcohol. Examples of the above plasticizer include concentrated glycerin and macrogol 400. Examples of the above coloring agent include titanium oxide, red ferric oxide, yellow ferric oxide and talc.

Further, the therapeutic or prophylactic agent for cachexia accompanied by ghrelin resistance can be produced by suitably using the above carrier by a typical method. A pharmaceutical composition containing the opioid κ receptor agonistic compound and the pharmacologically acceptable carrier can also be produced in the same manner.

Examples of dosage forms when the opioid κ receptor agonistic compound is orally administered as the therapeutic or prophylactic agent for cachexia accompanied by ghrelin resistance include a tablet, a capsule, an orally disintegrating agent, a powder and a granule, and examples of parenteral administration include intravenous rapid infusion, intravenous continuous infusion, intramuscular injection, subcutaneous injection, intracutaneous injection, an inhalant, an suppository, an ointment, a cream and a patch. Further, a known long-acting formulation is also acceptable.

The content of the opioid κ receptor agonistic compound in the above therapeutic or prophylactic agent for cachexia accompanied by ghrelin resistance is not particularly limited, but can be adjusted to contain typically 0.1 μg to 100 mg per dose. Additionally, the dosage can suitably be selected according to a patient's symptoms, age, sex, weight, administration method or the like and is typically preferably 0.1 μg to 20 mg, and more preferably 1 μg to 10 mg, in terms of an amount of the opioid κ receptor agonistic compound per adult per day. The dosage of the compound represented by General Formula (I) or a pharmacologically acceptable acid addition salt thereof is preferably 1 μg to 100 μg in terms of an amount of the compound or a pharmacologically acceptable acid addition salt thereof per adult per day. The dosage of the compound represented by General Formula (II) or a pharmacologically acceptable acid addition salt thereof is preferably 10 μg to 1 mg in terms of an amount of the compound or a pharmacologically acceptable acid addition salt thereof per adult per day. The dosage can be administered in one to several doses.

To complement or enhance the ameliorating effect or the prophylactic effect or reduce the dosage, the therapeutic or prophylactic agent for cachexia accompanied by ghrelin resistance can further be administered in combination with one or more drugs used to treat or prevent cachexia accompanied by ghrelin resistance or reduce or suppress symptoms. The drug to be combined may be a low molecular compound or a macromolecular protein, a polypeptide, an antibody or a vaccine. In this example, the therapeutic agent or the prophylactic agent can also be administered simultaneously with a drug(s) to be combined or at different times. The therapeutic agent or the prophylactic agent and the drug(s) to be combined may be used in combination, or they may be prepared in the form of a compound drug. The dosage of a drug(s) to be combined can suitably be selected based on the dose clinically used, respectively. Additionally, the combination ratio of the above therapeutic or prophylactic agent for symptoms of cachexia accompanied by ghrelin resistance to a drug(s) to be combined can suitably be selected according to a subject to be administered, age, weight, symptoms of a subject to be administered, dosing time, dosage form, administration method and the like.

The therapeutic or prophylactic agent for cachexia accompanied by ghrelin resistance can be preferably used as a therapeutic or prophylactic agent for cancer cachexia accompanied by ghrelin resistance (cachexia caused by malignant melanoma, malignant bone tumor, gastric cancer, hepatocyte cancer, acute myeloid leukemia, acute lymphocytic leukemia, uterine cervical cancer, uterine cancer, esophagus cancer, pancreatic cancer, prostate cancer, colorectal cancer, breast cancer, lung cancer, bladder cancer, and ovarian cancer, for example).

The therapeutic or prophylactic agent for cancer cachexia accompanied by ghrelin resistance can be preferably used as a therapeutic or prophylactic agent for cancer cachexia to which a GHSR agonist such as anamorelin would not respond.

In the method of treating or preventing cachexia accompanied by ghrelin resistance, the opioid κ receptor agonistic compound is administered to a patient in need of treatment or prevention of cachexia accompanied by ghrelin resistance. An example of a patient in need of treatment of cachexia accompanied by ghrelin resistance is a patient having the cachexia accompanied by ghrelin resistance mentioned above. It is preferable that a patient have cachexia to which a GHSR agonist such as anamorelin hydrochloride would not respond. It is more preferable that a patient exhibit increased ghrelin concentration in blood and have the cachexia to which a GHSR agonist such as anamorelin hydrochloride would not respond. An example of a patient in need of prevention of cachexia accompanied by ghrelin resistance is a patient having an underlying disease, which can cause the cachexia accompanied by ghrelin resistance. It is preferable that a patient have chronic diseases such as malignant tumors, tuberculosis, diabetes, blood diseases, endocrine diseases, infectious diseases, and acquired immunodeficiency syndrome. It is more preferable that a patient exhibit increased ghrelin concentration in blood and have the chronic disease as exemplified above.

EXAMPLES

Hereinafter, our agents and methods will be specifically described by way of Examples, but these should not be construed as limitations to this disclosure.

Example 1: Effect of (−)-17-(cyclopropylmethyl)-3,14β-dihydroxy-4,5α-epoxy-6β-[N-methyl-trans-3-(3-furyl)acrylamide]morphinan hydrochloride (Hereinafter, Referred to as Compound 1) in Tumor-Bearing Mouse Model (Non-Small Cell Lung Cancer Model Accompanied by Ghrelin Resistance)

Using tumor-bearing model animals where adenocarcinomic human alveolar basal epithelial cells, A549 cells, were transplanted into nude mice, examination was performed about drug efficacy of Compound 1 on the food intake and the body weight.

Subculture of A549 cells was performed using a 10% FBS-containing RPMI1640 culture medium. In evaluation of drug efficacy, 6-week-old female BALB/C slc/nu/nu mice (Japan SLC, Inc.) were purchased, and were used after habituated for one week. Tumor-bearing model animals were prepared as follows. Specifically, $2.5\times10^7$ cells of A549 cells were transplanted to the right abdominal region of each mouse by subdermal administration. On Day 43 from the cell transplantation, the mice were divided into groups to have an equal averaged tumor volume.

The effects of a variety of compounds on food intake and body weight were examined as follows. Specifically, for 5 days from Day 44 to Day 48 from the cell transplantation, the compounds were orally administered daily, and the food intake and the body weight were measured at the same time. The doses of Compound 1 were 0.25 mg/kg (6 animals), 0.5 mg/kg (6 animals), and 1 mg/kg (6 animals). To verify that the model animals are in a ghrelin resistant state, anamorelin hydrochloride (MedChemExpress) was used at 30 mg/kg (6 animals). The food intake was calculated by subtracting the weight of feed on the previous day of measurement from the weight of feed on the day of measurement.

Figure 2:
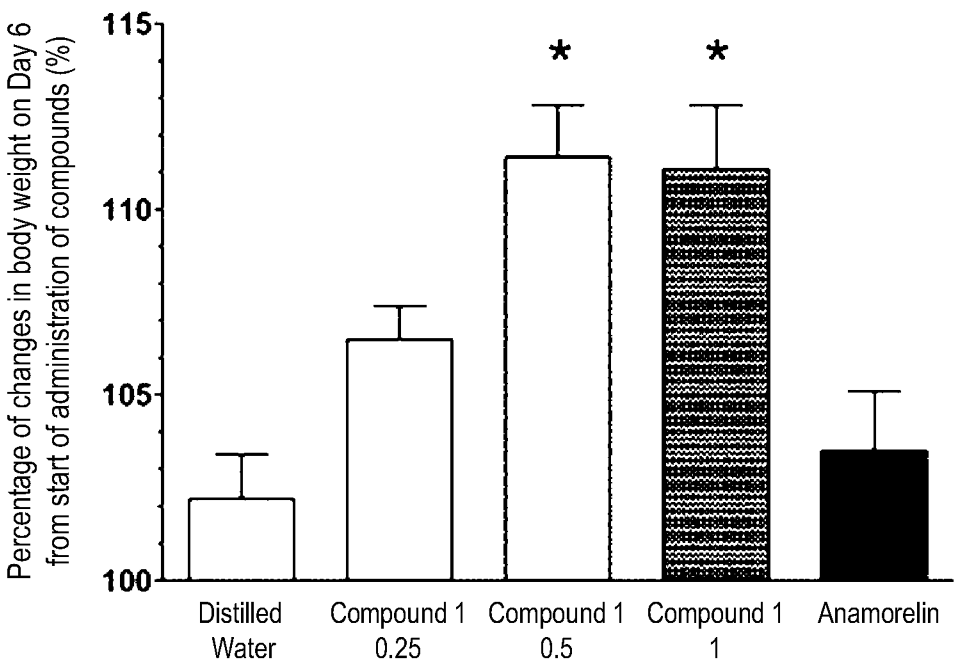
FIG. 2 is a graph showing the increasing effect in body weight by administration of Compound 1 in a tumor-bearing mouse model (non-small cell lung cancer model accompanied by ghrelin resistance).

The results are shown in FIGS. 1 and 2. In FIG. 1, the ordinate represents the cumulative food intake in the period of administration of the compounds (from the start of administration to the day next to the final day of administration). In FIG. 2, the ordinate represents the percentage of changes in body weight on Day 6 from the start of administration of the compounds (the day next to the final day of administration) (after 5-day administration) (relative to the body weight measured immediately before the first administration of the compound designated as 100%). In the abscissas of FIGS. 1 and 2, "Distilled water" represents distilled water-treated group, "Compound 1 0.25" represents Compound 1-treated group at 0.25 mg/kg, "Compound 1 0.5" represents Compound 1-treated group at 0.5 mg/kg, "Compound 1 1" represents Compound 1-treated group at 1 mg/kg, and "Anamorelin" represents anamorelin hydrochloride-treated group at 30 mg/kg. In FIGS. 1 and 2, the mark "*" represents a statistical significance (*: $P<0.05$) in comparison with distilled water-treated group (Dunnett's multiple test).

Concerning the cumulative food intake in the period of administration of the compounds, Compound 1 exhibited a statistically significant increasing effect in food intake in all the Compound 1-treated groups, in comparison with the distilled water-treated group. Concerning the body weight after the compounds had been administered for 5 days, Compound 1 exhibited a tendency of an increase in body weight at 0.25 mg/kg, and statistically significant increasing effect in body weight was observed in Compound 1-treated group at 0.5 mg/kg and in Compound 1-treated group at 1 mg/kg, in comparison with the distilled water-treated group. In the anamorelin hydrochloride-treated group, in contrast, any statistically significant increasing effect in food intake or increasing effect in body weight was not observed compared to the distilled water-treated group.

In the results above, anamorelin hydrochloride (administered at 30 mg/kg) did not exhibit effectiveness to the cumulative food intake and the body weight. This suggests that the tumor-bearing model animals had ghrelin resistance. Accordingly, Compound 1 was demonstrated to have the increasing effect in food intake and the increasing effect in body weight on cancer cachexia accompanied by ghrelin resistance.

Example 2: Effect of Compound Represented by Formula (II) (Hereinafter, Referred to as Compound 2) in Tumor-Bearing Mouse Model (Non-Small Cell Lung Cancer Model Accompanied by Ghrelin Resistance)

Using tumor-bearing model animals where adenocarcinoma human alveolar basal epithelial cells, A549 cells, were transplanted into nude mice, examination was performed about drug efficacy of Compounds 1 and 2 on the food intake and the body weight.

Subculture of A549 cells was performed using a 10% FBS-containing RPMI1640 culture medium. In evaluation of drug efficacy, 7-week old female BALB/C slc/nu/nu mice (Japan SLC, Inc.) were purchased, and were used after habituated for one week. Tumor-bearing model animals were prepared as follows. Specifically, $2.5\times10^7$ cells of A549 cells were transplanted to the right abdominal region of each mouse by subdermal administration. On Day 43 from the cell transplantation, the mice were divided into groups to have an equal averaged tumor volume.

The effects of a variety of compounds on food intake and body weight were examined as follows. Specifically, for 5 days from Day 44 to Day 48 from the cell plantation, Compound 2 was intraperitoneally administered daily, Compound 1 and anamorelin hydrochloride were orally administered daily, and the amount of feed and the body weight were measured at the same time. Compound 2 was used at 1 mg/kg (9 animals), and Compound 1 was used at 0.25 mg/kg (9 animals), which is the lowest dose to exert drug efficacy. To verify that the model animals are in a ghrelin resistant state, anamorelin hydrochloride was used at 30 mg/kg (9 animals) herein. The food intake was calculated by subtracting the weight of feed on the previous day of measurement from the weight of feed on the day of measurement.

Figure 3:
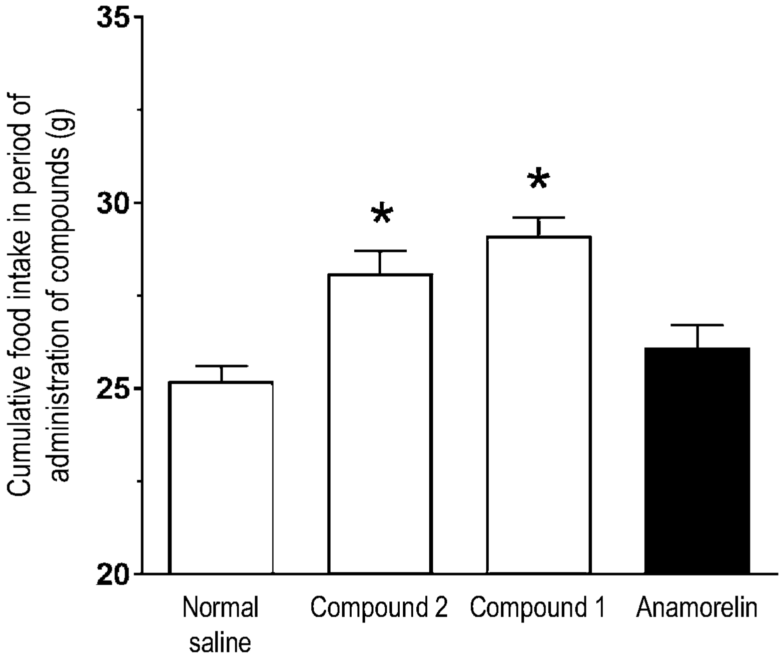
FIG. 3 is a graph showing the increasing effect in cumulative food intake by administration of Compound 2 in a tumor-bearing mouse model (non-small cell lung cancer model accompanied by ghrelin resistance).
Figure 4:
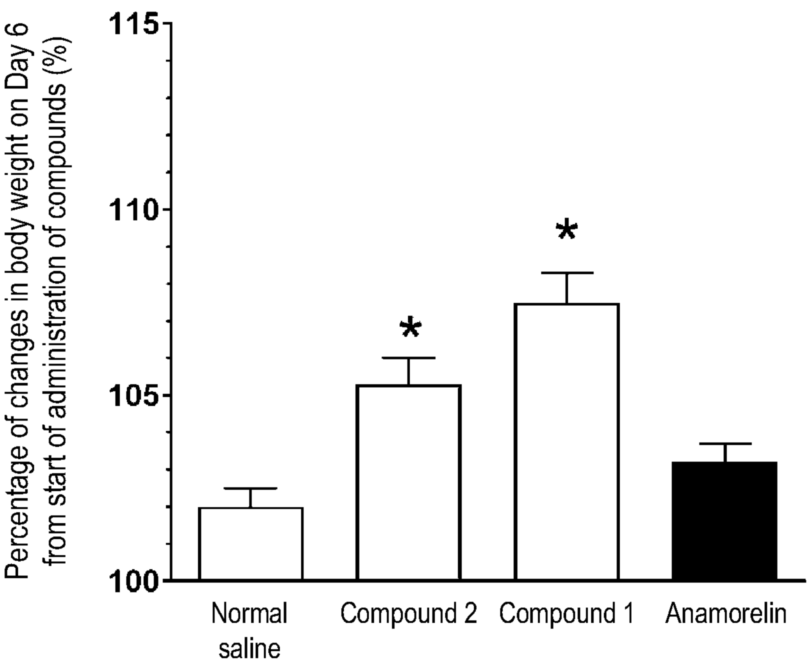
FIG. 4 is a graph showing the increasing effect in body weight by administration of Compound 2 in a tumor-bearing mouse model (non-small cell lung cancer model accompanied by ghrelin resistance).

The results are shown in FIGS. 3 and 4. In FIG. 3, the ordinate represents the cumulative food intake in the period of administration of the compounds (from the start of administration to the day next to the final day of administration). In FIG. 4, the ordinate represents the percentage of changes in body weight on Day 6 from the start of administration of the compounds (the day next to the final day of administration) (after 5-day administration) (relative to the body weight measured immediately before the first administration of the compound designated as 100%). In the abscissas of FIGS. 3 and 4, "Normal saline" represents a group treated intraperitoneally with normal saline, "Compound 2" represents a group treated intraperitoneally with Compound 2 at 1 mg/kg, "Compound 1" represents a group treated orally with Compound 1 at 0.25 mg/kg, and "Aanamorelin" represents a group treated orally with anamorelin hydrochloride at 30 mg/kg. In FIGS. 3 and 4, the mark "*" represents a statistical significance (*: $P<0.05$) compared to the group treated with normal saline (Dunnett's multiple test).

For the cumulative food intake in the period of administration of the compounds, Compound 2 exhibited a statistically significant increasing effect in food intake, in comparison with the group treated with normal saline. Concerning the body weight after Compound 2 had been administered for 5 days, Compound 2 exhibited statistically significant increasing effect in body weight, in comparison with the group treated with normal saline. In contrast, Compound 1 exhibited the increasing effect in food intake and the increasing effect in body weight higher than those exhibited by Compound 2.

The above results demonstrate that the opioid κ receptor agonistic compound exerts significant therapeutic effects on cachexia accompanied by ghrelin resistance.

In Example 2, Compound 2 is administered at the maximal dose that would not cause side effects caused by action of the opioid κ receptor (e.g., sedation). Thus, the dose thereof cannot be increased any more, and higher therapeutic effects cannot be expected. Accordingly, the compound represented by General Formula (I) or a pharmacologically acceptable acid addition salt thereof was found to exert more potent therapeutic effects on cachexia accompanied by ghrelin resistance than the compound represented by Formula (II) or a pharmacologically acceptable acid addition salt thereof.

Example 3: Measurement of Ghrelin (Acylated Ghrelin) Concentration in Blood of Tumor-Bearing Mouse Model The same tumor-bearing mouse models as used in Examples 1 and 2 were used, and the ghrelin concentration in plasma was measured.

The tumor-bearing mouse models were prepared in accordance with Example 2. The tumor-bearing mouse models are reported to have achieved therapeutic effects on cachexia when anamorelin hydrochloride was administered on Day 23 from the cell transplantation (Support Care Cancer, 2013, Vol. 21, pp. 2409-2415). When anamorelin hydrochloride was administered from Day 44 after the cell plantation, no therapeutic effects were observed on cachexia, as demonstrated in Examples 1 and 2. It is thus considered that ghrelin resistance was not developed on Day 23 from cell transplantation and ghrelin resistance was developed on Day 44 from cell transplantation in the tumor-bearing models. Specifically, the ghrelin concentration in plasma is deduced to be higher on Day 44 from the cell transplantation after ghrelin resistance has developed, compared with the ghrelin concentration in plasma up to Day 23 from the cell transplantation before ghrelin resistance is developed. Accordingly, the same model was used to measure the ghrelin concentration in plasma at two points; i.e., on Days 20 and 44 from the cell transplantation herein. The plasma samples were obtained by blood sampling from the jugular vein, followed by centrifugation. The ghrelin concentration was measured using a commercialized assay kit (Bertin Bioreagent). In blood sampling, a protease inhibitor was used, and hydrochloric acid was added after the plasma samples were obtained to stabilize the samples.

As a result, the ghrelin concentration in plasma was 74.5 pg/ml on Day 20 from cell plantation, and it was 195 pg/ml on Day 43 from cell plantation. That is, the ghrelin concentration in blood was higher in a model that had developed ghrelin resistance (a period after cell plantation).

The above results demonstrate that ghrelin concentration in blood is high in the ghrelin resistance models used in evaluation in Examples 1 and 2, as in the report on humans.

INDUSTRIAL APPLICABILITY

Our therapeutic or prophylactic agent for cachexia accompanied by ghrelin resistance has a high therapeutic effect to cachexia accompanied by ghrelin resistance, and thus is useful in the medical drug field.

All the publications, Patents, and Patent applications cited in this specification, as they are, are incorporated in this specification by reference.

This specification encompasses the contents of the description and/or the drawings described in Japanese Patent Application No. 2021-73026, on which the priority of this application is based.

The invention claimed is:

1. A method of treating er preventing cachexia accompanied by ghrelin resistance, the method comprising a step of administering an opioid κ receptor agonistic compound to a patient in need of treatment of cachexia accompanied by ghrelin resistance, wherein the opioid κ receptor agonistic compound is a compound represented by General Formula (I) or (II) or a pharmacologically acceptable acid addition salt thereof:

(I)

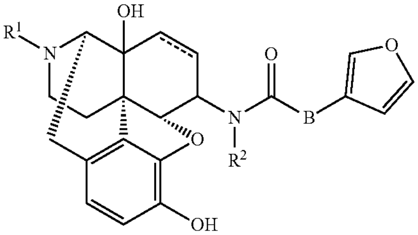

(II)

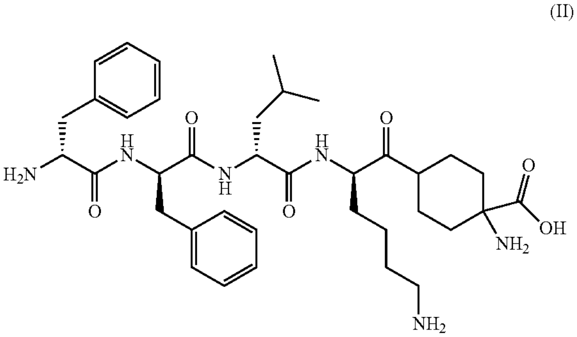

wherein a double line composed of a dotted line and a solid line represents a double bond or a single bond, $R^1$ represents a cycloalkylalkyl having 4 to 7 carbon atoms, $R^2$ represents a linear or branched alkyl having 1 to 5 carbon atoms, and B represents a —CH═CH—.

2. The method according to claim 1, wherein $R^1$ is a cyclopropylmethyl, a cyclobutylmethyl, a cyclopentylmethyl, or a cyclohexylmethyl, and $R^2$ is a methyl, an ethyl, or a propyl.

3. The method according to claim 1, wherein $R^1$ is a cyclopropylmethyl, $R^2$ is a methyl, and B is a trans-form —CH═CH—.

4. The method according to claim 1, wherein the compound represented by General Formula (I) is (−)-17-(cyclopropylmethyl)-3,14β-dihydroxy-4,5α-epoxy-6β-[N-methyl-trans-3-(3-furyl)acrylamide]morphinan represented by:

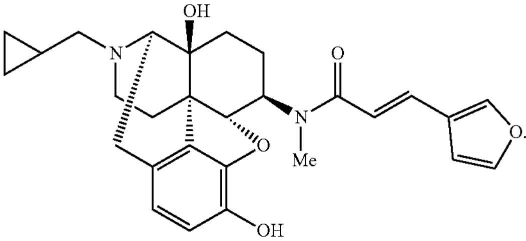

5. The method according to claim 1, wherein the cachexia is cancer cachexia.

* * * * *